United States Patent [19]

Mito et al.

[11] Patent Number: 5,596,135
[45] Date of Patent: Jan. 21, 1997

[54] APPARATUS FOR AND METHOD OF DETERMINING PURITY OF A PEAK OF A PEAK OF A CHROMATOGRAM

[75] Inventors: Yasuhiro Mito; Hideki Minegishi, both of Kyoto, Japan

[73] Assignee: Shimadzu Corporation, Nakagyo-ku, Japan

[21] Appl. No.: 373,573

[22] Filed: Jan. 13, 1995

[30] Foreign Application Priority Data

Jan. 31, 1994 [JP] Japan .................... 6-029043

[51] Int. Cl.$^6$ ................................ G01N 30/02
[52] U.S. Cl. ......................... 73/23.35; 364/498
[58] Field of Search .............. 73/23.35, 23.36, 73/23.37; 364/498

[56] References Cited

U.S. PATENT DOCUMENTS

| | | | |
|---|---|---|---|
| 3,863,489 | 2/1975 | Ayers et al. | 73/23.36 |
| 4,353,242 | 10/1982 | Harris et al. | 73/23.36 |
| 4,482,966 | 11/1984 | Mito et al. | 364/498 |
| 4,740,903 | 4/1988 | Nakatsuka et al. | 73/23.36 |
| 4,807,148 | 2/1989 | Lacey | 73/23.36 |
| 4,835,708 | 5/1989 | Frans | 73/23.5 |
| 4,885,697 | 12/1989 | Hubner | 364/497 |
| 5,121,337 | 6/1992 | Brown | 364/498 |
| 5,227,986 | 7/1993 | Yokota et al. | 364/498 |
| 5,313,406 | 5/1994 | Kauppinen et al. | 364/498 |
| 5,400,265 | 3/1995 | Kauppinen | 364/498 |
| 5,446,681 | 8/1995 | Gethner et al. | 364/554 |

FOREIGN PATENT DOCUMENTS

| | | |
|---|---|---|
| 57-139647 | 8/1982 | Japan . |
| 1-161123 | 6/1989 | Japan . |

*Primary Examiner*—Hezron E. Williams
*Assistant Examiner*—Jay L. Politzer
*Attorney, Agent, or Firm*—Oliff & Berridge

[57] ABSTRACT

It is judged whether a part of a peak section of a chromatogram corresponding to a component of a sample is pure by comparing a similarity value of the absorbance spectrum of the part to a threshold value. The similarity value r and the threshold value t are calculated as follows. a) A series of absorbance spectra of a sample effluent from a column of the chromatograph are obtained repeatedly at a plurality of time points of short intervals. An absorbance spectrum is composed of a set of absorbance data with respect to wavelengths of light passing through the sample. b) A chromatogram of the sample is constructed using the series of absorbance spectra. c) A peak section including an object component of the sample is detected in the chromatogram. d) A similarity value is then calculated as a cosine of the angle between an absorbance spectrum vector and a standard spectrum vector. e) The threshold value is calculated by a cosine of the angle between two outermost tangential lines of an n-dimensional sphere centering an end of the absorbance spectrum vector and another n-dimensional sphere centering an end of the standard spectrum vector.

18 Claims, 5 Drawing Sheets

RELATED ART

APPARATUS FOR AND METHOD OF DETERMINING PURITY OF A PEAK OF A PEAK OF A CHROMATOGRAM

The present invention relates to a chromatograph such as a high performance liquid chromatograph (HPLC), and especially to its detector for obtaining a series of absorbance spectra of a sample effluent from a column of the chromatograph and for analyzing the data of the absorbance spectra.

BACKGROUND OF THE INVENTION

When two peaks corresponding to distinct components are very close and are not fully separate in a chromatogram, a comparative chromatogram method is used. In the comparative chromatogram method, an index P is calculated by the following equation (1) using absorbance values $A(\lambda_1)$, $A(\lambda_2)$ and background values $A_B(\lambda_1)$, $A_B(\lambda_2)$ at two preset wavelengths $\lambda_1$ and $\lambda_2$ in every absorbance spectrum detected repeatedly on the mobile phase effluent from the column.

$$P = \{A(\lambda_1) - A_B(\lambda_1)\} / \{|A(\lambda_1) - A_B(\lambda_1)|^2 + |A(\lambda_2) - A_B(\lambda_2)|^2\}^{1/2} \quad \ldots \quad (1)$$

The index P has the following meaning. Let us introduce a vector aa having components $(a_1, a_2)$ which are given as follows.

$$A(\lambda_1) - A_B(\lambda_1) = a_1$$

$$A(\lambda_2) - A_B(\lambda_2) = a_2$$

Using the vector aa, the equation (1) is rewritten as $$P = a_1 / |aa|$$

This means that the index P represents the cosine of the angle $\theta$ (i.e., $\cos\theta$) between the vector $aa(a_1, a_2)$ and a vector $(a_1, 0)$ as shown in FIG. 7.

When the mobile phase (or solvent) alone is flowing out of the column, $A(\lambda_1) = A_B(\lambda_1)$ and $A(\lambda_2) = A_B(\lambda_2)$ because what is detected is the background only. Thus, $a_1 = a_2 = 0$ and the vector aa is a zero vector. When a peak in a chromatogram is a simple peak corresponding to a single component as shown at the left of the top $\lambda_1$–$\lambda_2$ curves of FIG. 8, the direction of the vector aa is unchanged though the length thereof varies because the ratio of values of $a_1$ and $a_2$ is constant. That is, the vector aa moves within the linear region $P_1$ shown in FIG. 7, and the value of index P (=$\cos\theta$) is constant as shown at the left of the bottom curve of FIG. 8.

When, on the other hand, a peak is complex and corresponds to plural different components as shown at the right of the top $\lambda_1$–$\lambda_2$ curves of FIG. 8, the ratio of the absorbance values at the wavelengths $\lambda_1$ and $\lambda_2$ changes with respect to time. Thus the vector aa moves two-dimensionally within a region $P_2$ as shown in FIG. 7, and the value of index P changes as shown at the right of the bottom curve of FIG. 8.

That is, in the comparative chromatogram method, a peak is judged to be simple or complex by detecting whether the value of index P changes with respect to time.

However, the comparative chromatogram method has following drawbacks.

(i) The value of index P cannot be absolutely constant since, in equation (1), the absorbance at the preset two wavelengths $A(\lambda_1)$, $A(\lambda_2)$ are subtracted by respective background values $A_B(\lambda_1)$, $A_B(\lambda_2)$, and every measured absorbance generally includes incessant fluctuation or noise. Thus, conventionally, an operator empirically sets a tolerance for the index P depending on the apparatus, and it is assumed that variation in the value of index P within the tolerance is due to noise.

(ii) It is necessary to determine beforehand in chromatography a critical concentration (percentage) of impurities which can be definitely detected. In the comparative chromatogram method, it is difficult to determine a definite critical value beforehand because of the reason above.

(iii) When an object component is desired to be separated from a sample, a column chromatograph is used. If an impurity having a retention time close to the object component is included in the sample, the separation is difficult. But if such a period in the retention time that includes the impurity is known, the separation becomes possible. Conventional methods cannot teach such a period.

SUMMARY OF THE INVENTION

The present invention is achieved to overcome the above drawbacks in the conventional method. Thus a detector for a chromatograph according to the present invention comprises:

a) spectra obtaining device for obtaining a series of absorbance spectra of a sample effluent from a column of the chromatograph repeatedly obtained at a plurality of time points separated by short intervals, an absorbance spectrum being composed of a set of absorbance data with respect to wavelengths of light passing through the sample;

b) chromatogram constructing device for constructing a chromatogram of the sample using the series of absorbance spectra;

c) peak section detecting device for detecting a peak section including an object component of the sample in the chromatogram;

d) similarity calculating device for calculating a similarity value between an absorbance spectrum of every time point and a standard absorbance spectrum of the object component;

e) threshold calculating device for calculating a threshold value using the absorbance spectrum of every time point, the standard absorbance spectrum and a noise level value of the chromatograph; and f) determining device that determines whether the absorbance spectrum is similar to the standard absorbance spectrum by comparing the similarity value to the threshold value.

The similarity calculation, threshold calculation and judgement may be made only within the peak section including the object component for time efficiency. Details and other features of the present invention are described in the following description of a preferred embodiment.

DETAILED DESCRIPTION OF A PREFERRED EMBODIMENT

Figure 1:
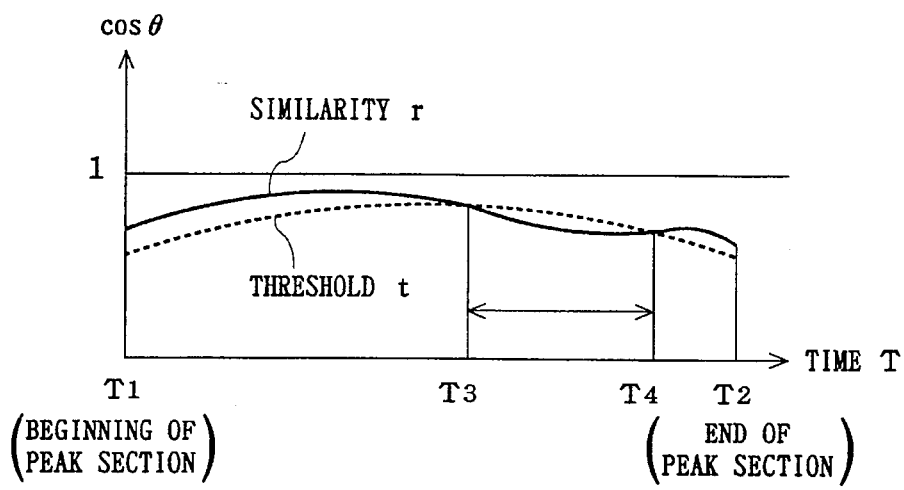
FIG. 1 is an example of a graph of similarity r and threshold t with respect to time.
Figure 2:
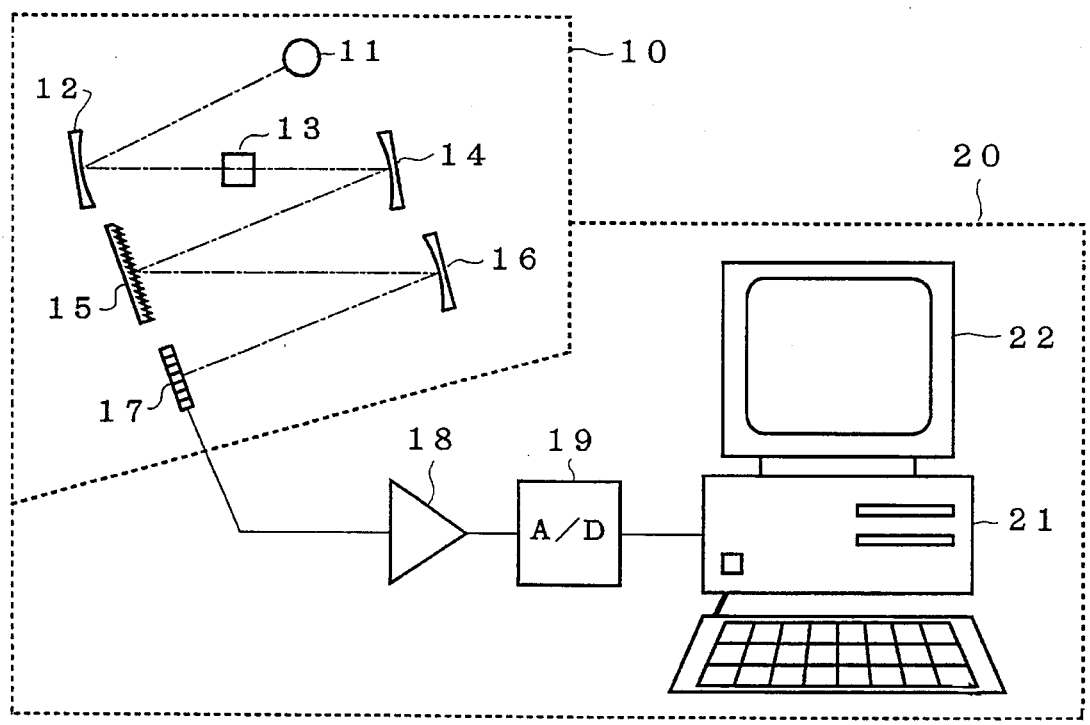
FIG. 2 is a schematic plan view of a spectral optical system and signal analyzing section of an embodiment of the present invention.

A detector for a high performance liquid chromatograph (HPLC) embodying the present invention is described using FIGS. 1 through 6. As shown in FIG. 2, the detector of the present embodiment is composed of a spectral optical system 10 and a signal analyzing section 20. In the spectral optical system 10, a light source 11 casts white light at a flow cell 13 via a reflection mirror (concave mirror) 12. In passing the flow cell 13, the white light undergoes absorption at wavelengths proper to the components included in the sample. The light that has passed the flow cell 13 is cast to a diffraction grating 15 via another reflection mirror (concave mirror) 14 where the light is separated into a spectrum. The separated light is further reflected by a third reflection mirror (concave mirror) 16 and the strength of the light at every wavelength is detected by a photo-diode array detector 17. In the present invention, any type of spectral optical system 10 can be used instead of that described above if a spectrum of the light that has passed the sample is obtained. For example, a prism can be used instead of the diffraction grating, or a high speed scanning spectral detector can be used instead of the light separating element and the spectrum detector.

The detection signal generated in every photo-diode element of the photo-diode array detector 17 is sent to an A/D converter 19 via an amplifier 18 of the signal analyzing section 20, where the signal is converted to digital data representing the strength of the light at the corresponding wavelength. The spectrum data thus obtained is sent to a personal computer 21, where it is converted to absorbance spectrum data and the following data analysis is performed.

Figure 3:
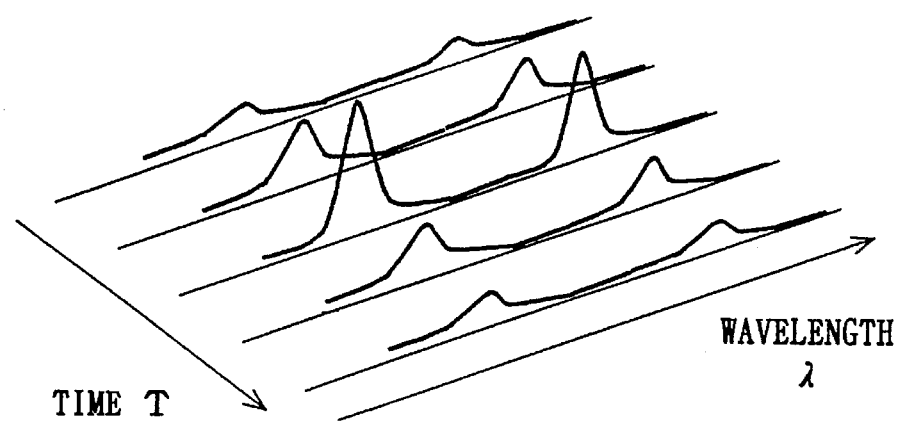
FIG. 3 is a three-dimensional graph of a series of absorbance spectra.
Figure 5A:
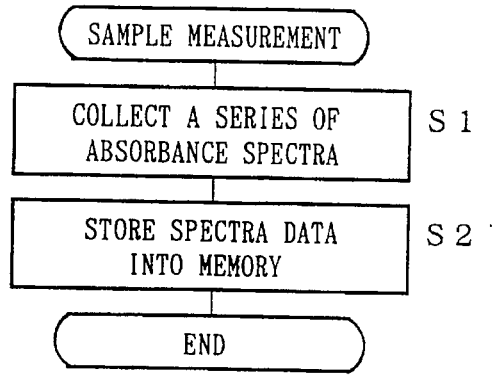
FIG. 5A is a flowchart of data collecting process.
Figure 5B:
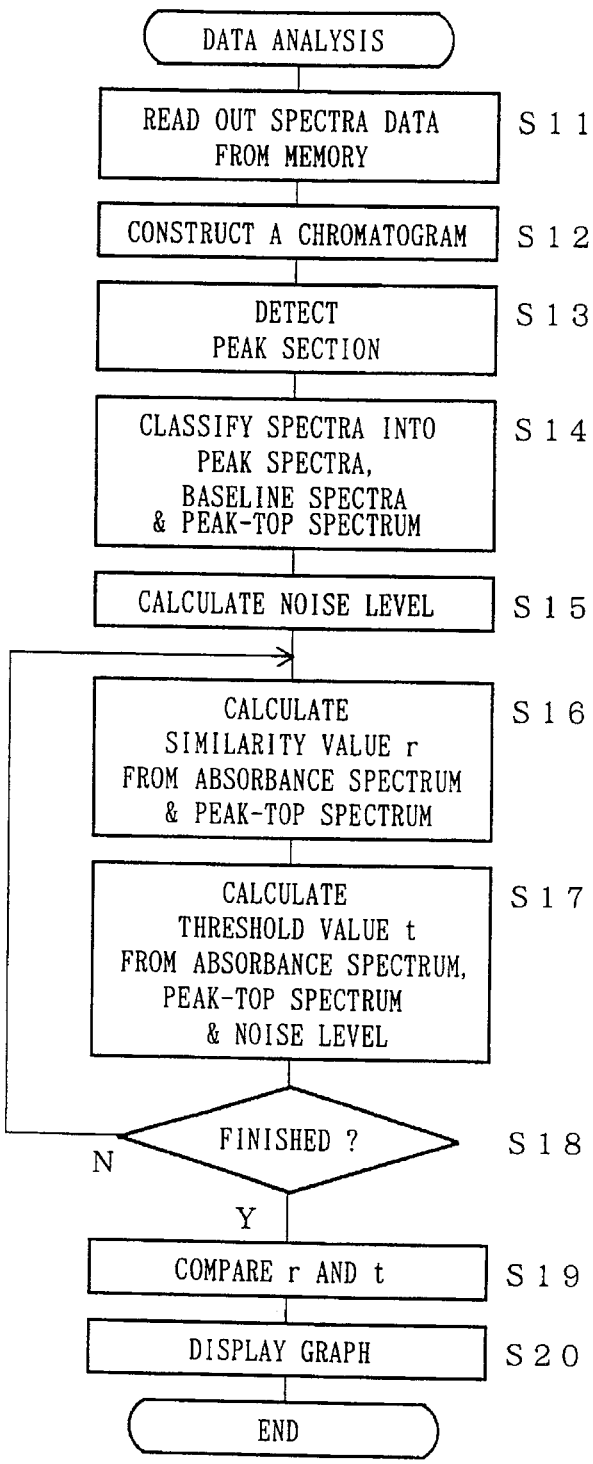
FIG. 5B is a flowchart of data analyzing process.

The process of collecting and analyzing data performed in the analyzing section 20 is described using the flowcharts of FIGS. 5A and 5B. After a sample is injected at an injector of the HPLC (not shown), the A/D converter 19 is effected for a preset period encompassing the retention time of the components included in the sample. During the period, a series of absorbance spectra described above are collected at regular short intervals (step S1) as shown in FIG. 3. The data of the absorbance spectra is stored into an internal memory (RAM) or into an external memory (such as a hard disk) of the personal computer 21 (step S2). When the preset period ends, the data collection process of FIG. 5A ends.

Then the personal computer 21 processes data of all the absorbance spectra collected within the period and stored in the memory according to the flowchart of FIG. 5B. First, all the absorbance spectra are read out from the memory (step S11), and a chromatogram is constructed by plotting the sum of the absorbance values within a specified wavelength range in a spectrum against the retention time of the spectrum (step S12). Then peak sections are detected from the chromatogram (step S13). Conventional methods can be used here to detect a peak section of a chromatogram. For example, a peak section is judged to begin when the tangent of the chromatogram curve exceeds a preset beginning slope value, and the peak section is judged to end when the tangent subsides below a preset ending slope value. The beginning slope value and the ending slope value may be equal or different.

The spectra read out from the memory are then classified into a group of peak spectra and a group of baseline spectra (step S14). Peak spectra are such absorbance spectra that fall within the peak sections, and baseline spectra are such absorbance spectra that fall outside of the peak sections. It is possible to define the baseline spectra otherwise. For example, baseline sections are defined independently from the peak section using another slope value smaller than that used to define the beginning of peak (or than that used to define the end of peak), and those absorbance spectra that fall within the baseline sections are defined as baseline spectra. This method of different slope standards for the peak section and for the baseline section can decrease the influence of peak data on the baseline data. It is still possible to collect the baseline data by measuring the same mobile phase by itself without injecting sample. After the absorbance spectra are classified into peak spectra and baseline spectra, a peak-top spectrum is picked up from the peak spectra of each peak section (step S14).

Figure 4:
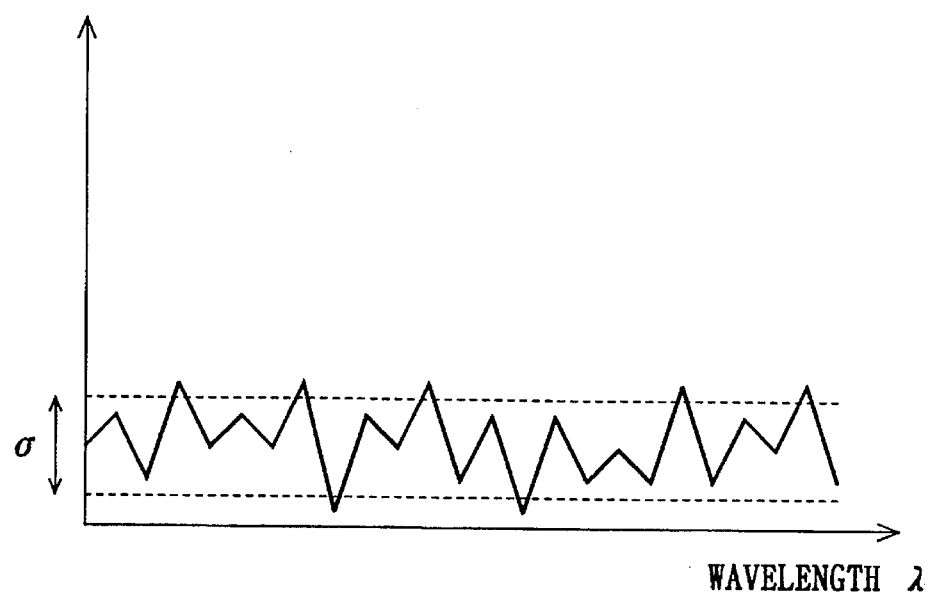
FIG. 4 is a graph of a part of absorbance spectrum including only noise.

Then the noise level N is calculated from the baseline spectra (step S15). The standard deviation $\sigma$ (or $3\cdot\sigma$ instead) of all the values in a baseline spectrum or of all the baseline spectra can be used as the noise level N (FIG. 4). It is noted that the result of judgement described below changes according to the assumption of the noise level, so that the noise level assumption of $\sigma$ and noise level assumption of $3\cdot\sigma$ may bring about different judgement at certain critical points.

Next, the peak spectra that fall within a peak section including an object component are read out from the memory one by one, and a similarity r and a threshold t are calculated on every peak spectrum belonging to the peak section. If several peak sections are detected at step S13, the peak section corresponding to the object component is detected as such that includes the retention time of the object component. First, the absorbance spectrum of a first time point T in the present peak section is read out from the memory and a similarity r is calculated from the absorbance spectrum and the peak-top spectrum of the present peak section (step S16). A threshold t is calculated from the peak spectrum, the peak-top spectrum and the noise level N (step S17).

Figure 6A:
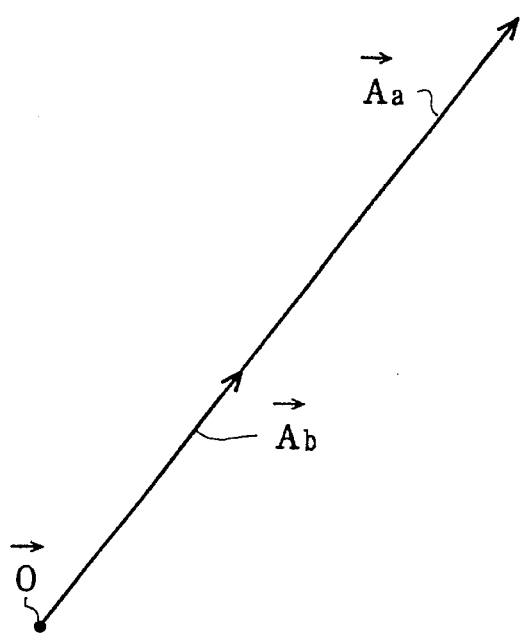
FIGS. 6A through 6C are vector diagrams explaining the derivation of similarity r and threshold t.
Figure 6B:
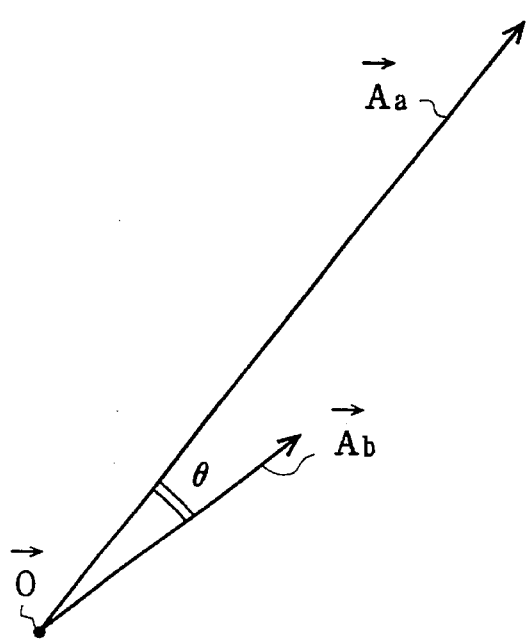
Figure 6C:
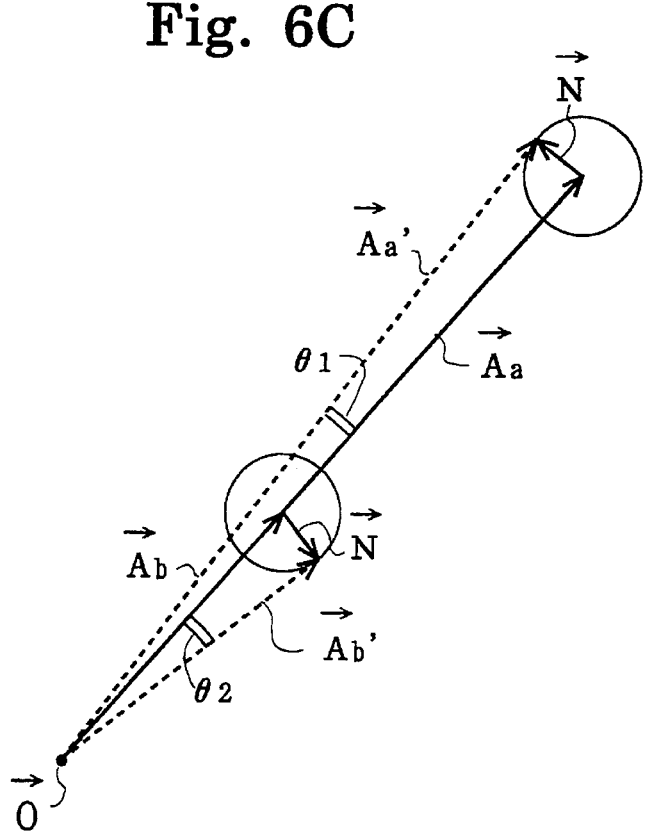
Figure 7:
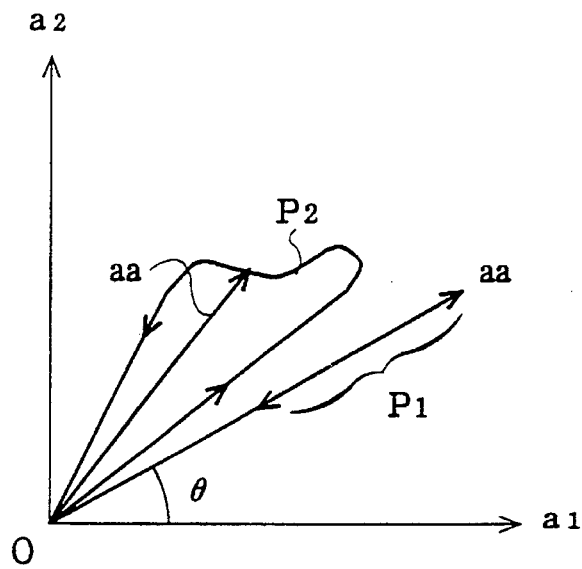
FIG. 7 is a vector diagram showing the movement of absorbance spectrum vectors.
Figure 8:
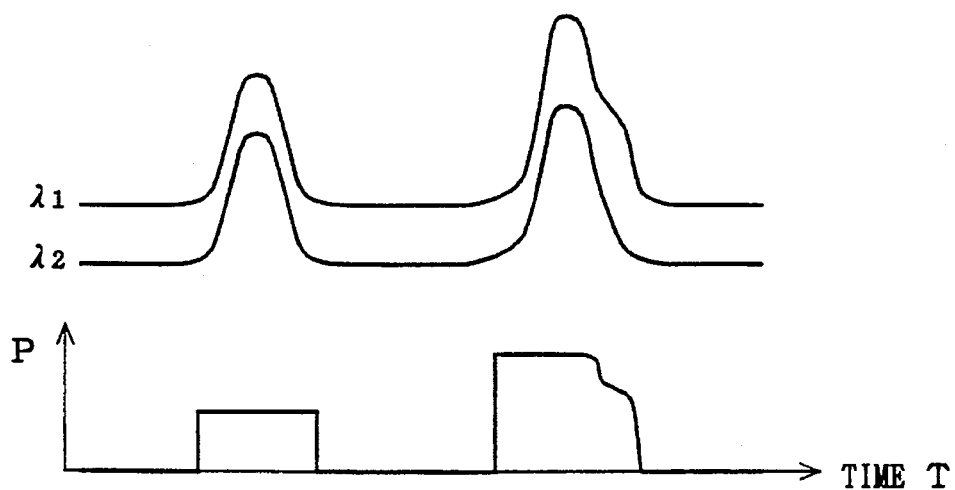
FIG. 8 is a time chart of chromatograms at wavelengths $\lambda_1$ and $\lambda_2$ and index P.

The similarity r and the threshold t are calculated as follows (which is also described in the Japanese laid open patent application No. H01-161123). It is assumed first that no noise is included, and supposed that the absorbances at wavelengths $\lambda_1, \lambda_2, \ldots, \lambda_n$ are $A_1, A_2, \ldots, A_n$, whereby the absorbance spectrum is represented by an n-dimensional vector $A(A_1, A_2, \ldots, A_n)$. When two absorbance spectra a and b come from the same sample, the ratios of corresponding components of the two vectors $Aa(Aa(\lambda_1), Aa(\lambda_2), \ldots, Aa(\lambda_n))$ and $Ab(Ab(\lambda_1), Ab(\lambda_2), \ldots, Ab(\lambda_n))$ which represent the two absorbance spectra a and b are respectively equal. That is, when $Aa(\lambda_1)/Ab(\lambda_1)=Aa(\lambda_2)/Ab(\lambda_2)=\ldots=Aa(\lambda_n)/Ab(\lambda_n)$, the two vectors Aa and Ab have the same direction in the n-dimensional space as shown in FIG. 6A. In FIGS. 6A–6C, the vector O is an origin vector of n-space. In other words, the angle $\theta$ between the two vectors Aa and Ab is zero. If, on the other hand, the two absorbance spectra a and b come from different samples, the ratios of corresponding components of the two vectors Aa and Ab are not equal. That is, the vectors Aa and Ab have different directions in the n-dimensional space, and the angle $\theta$ between them has a non-zero value.

Then the similarity r is defined by the following formula.

$$r = \cos\theta = (Aa \cdot Ab)/\{|Aa| \times |Ab|\} \quad (2)$$

where (Aa·Ab) is the inner product of the two vectors Aa and Ab. The similarity r is unity (1) when the two vectors have the same direction, and is close to unity (1) when their directions are close (that is, the angle θ between them is close to zero). Thus, two absorbance spectra can be judged to come from the same sample when the similarity r is close to 1, and they are judged to come from different samples when the value r is not close to 1.

It is rare, actually, that the two vectors coming from the same sample have exactly the same direction and the similarity r has an exact unity value, due to noises included in the measured absorbance data. Assuming a certain level of background noise, then, a criteria for the similarity r should be introduced to judge that two absorbance spectra come from the same sample. When no noise is included, the direction of two vectors Aa and Ab corresponding to two absorbance spectra a and b coming from a sample is the same as shown in FIG. 6B. When noise is included in the measured signals, as generally is, different noise vectors ($N_1$, $N_2$, ..., $N_n$) and ($N'_1$, $N'_2$, ..., $N'_n$) are added to respective Vectors Aa and Ab, whereby the vector corresponding to the absorbance spectrum a is represented by ($Aa(\lambda_1)+N_1$, $Aa(\lambda_2)+N_2$, ..., $Aa(\lambda_n)+N_n$), and the vector corresponding to the absorbance spectrum b is represented by ($Ab(\lambda_1)+N'_1$, $Ab(\lambda_2)+N'_2$, ..., $Ab(\lambda_n)+N'_a$). Assuming that the maximum of the absolute value of the noise vector is |N|, the end of each vector falls within an n-dimensional sphere of radius |N| with the center at the end of each vector Aa and Ab. When, therefore, the angle θ between two vectors Aa and Ab corresponding to two measured absorbance spectra a and b is larger than an angle ($\theta_1+\theta_2$) which is the angle between the outermost tangential lines of the two spheres as shown in FIG. 6C, it can be judged that there is no possibility that the two measured absorbance spectra a and b come from the same sample. Since the similarity r is defined by the cosine of the angle θ of the two vectors, as described above, the threshold t of the similarity r is also defined by the cosine of the angle ($\theta_1+\theta_2$). In particular, the threshold t is given by the following formula.

$$\begin{aligned} t &= \cos(\theta_1 + \theta_2) \quad (3) \\ &= \cos\theta_1 \times \cos\theta_2 - \sin\theta_1 \times \sin\theta_2 \\ &= \{(|Aa|^2 - |N|^2)^{1/2}/|Aa|\} \times \{(|Ab|^2 - |N|^2)^{1/2}/|Ab|\} - \\ & \quad (|N|/|Aa|) \times (|N|/|Ab|) \end{aligned}$$

Using the threshold t, it is judged that two absorbance spectra do not come from the same sample when r<t.

The similarity r between an absorbance spectrum and the peak-top spectrum of the present peak section and the threshold t are thus calculated using formulae (2) and (3) at steps S16 and S17. Then it is judged at step S18 whether the values r and t are calculated for all the absorbance spectra of the present peak section corresponding to the object component of the sample. When any data remains, the same calculations are performed on the next absorbance spectrum at the time point T+ΔT at steps S16 and S17. When all the absorbance spectra in the present peak section are processed, the time period $T_3-T_4$ is defined within which the similarity value r is smaller than the threshold value t at step S19. Further, the values of similarity r and threshold t are plotted against time T in the present peak section $T_1-T_2$ and the graph is presented on the display 22 of the personal computer 21 as shown in FIG. 1 (step S20).

The calculated results are used in various ways. An example is as follows. In the period $T_3-T_4$ where r<t, there is no possibility that the measured absorbance spectrum is the same as the absorbance spectrum of the object component (which is represented by the absorbance spectrumat the peak-top) even the maximum noise level is taken into account. Thus, purer object component can be separated from the sample by avoiding the period (or periods) $T_3-T_4$.

Another usage is that it can be used to determine the detection limit of a chromatograph. The detection limit of a chromatograph is defined as the amount of impurity component included in a sample and having the retention time close to that of an object component to which amount the impurity component can be discriminated. When a sample including a pure object component is measured, the similarity r exceeds the threshold t at every point of the peak section $T_1-T_2$ in the graph of FIG. 1. As the amount of such an impurity component is increased in the sample and when the amount exceeds a critical value c1, the period $T_3-T_4$ emerges in which r<t. The critical amount c1 of the impurity can be used as the detection limit of the chromatograph.

Though the peak-top spectrum is used as the standard spectrum of the object component in the above embodiment, it is possible to use another standard absorbance spectrum by measuring a standard sample including the object component alone.

Since the maximum noise level |N| is derived from the baseline section in the present embodiment (step S15) and the similarity judgement is performed automatically and objectively (steps S16–S19), no skilled operator is necessary.

What is claimed is:

1. A detector for a chromatograph comprising:
   a) means for obtaining a series of absorbance spectra of a sample effluent from a column of the chromatograph repeatedly obtained at a plurality of time points separated by short intervals during a retention time of the sample effluent, each absorbance spectrum of the series of absorbance spectra being composed of a set of absorbance data with respect to wavelengths of light passing through the sample effluent;
   b) means for constructing a chromatogram of the sample using the series of absorbance spectra;
   c) means for detecting a peak section including an object component of the sample effluent in the chromatogram in real time;
   d) means for calculating a similarity value between an absorbance spectrum of each of the plurality of time points and a standard absorbance spectrum of the object component, wherein the similarity calculating means calculates the similarity value based on an angle between an absorbance spectrum vector corresponding to the absorbance spectrum and a standard spectrum vector corresponding to the standard absorbance spectrum in real time;
   e) means for calculating a threshold value using the absorbance spectrum of said each of the plurality of time points, the standard absorbance spectrum and a noise level value of the chromatograph in real time; and
   f) means for determining whether the absorbance spectrum is similar to the standard absorbance spectrum by comparing the similarity value to the threshold value in real time.

2. The chromatographic detector according to claim 1, wherein the similarity calculating means calculate the similarity value by a cosine of the angle between the absorbance spectrum vector corresponding to the absorbance spectrum and the standard spectrum vector corresponding to the standard absorbance spectrum.

3. The chromatographic detector according to claim 1, wherein the threshold calculating means calculates the threshold value by a cosine of an angle between two outermost tangential lines of an n-dimensional sphere centering an end of the absorbance spectrum vector and another n-dimensional sphere centering an end of the standard spectrum vector.

4. The chromatographic detector according to claim 1, wherein the noise level value used in calculating the threshold value in the threshold calculating means is obtained from a statistical standard deviation of absorbance values of a baseline section of the chromatogram, the baseline section being a section or sections of the chromatogram excluding a peak section or peak sections.

5. The chromatographic detector according to claim 1, wherein the noise level value used in calculating the threshold value in the threshold calculating means is obtained from the absorbance values of a baseline section of a chromatogram obtained from a blank sample excluding the object component.

6. The chromatographic detector according to claim 1, wherein an absorbance spectrum at a top of the peak section is used as the standard absorbance spectrum.

7. The chromatographic detector according to claim 1, wherein the peak section detecting means detect a beginning of the peak section when a slope of the chromatogram exceeds a preset value and detect an end of the peak section when the slope of the chromatogram subsides below another preset value.

8. The chromatographic detector according to claim 7, wherein the noise level value used in calculating the threshold value in the threshold calculating means is obtained from a statistical standard deviation of absorbance values of a baseline section of the chromatogram, the baseline section being a section or sections of the chromatogram detected by using smaller threshold slope values than those used in detecting the peak section.

9. The chromatographic detector according to claim 1, wherein the determining means determines a detection limit of the chromatograph.

10. A method of determining purity of a peak of a chromatogram comprising the steps of:

a) obtaining a series of absorbance spectra of a sample effluent from a column of the chromatograph repeatedly at a plurality of time points separated by short intervals during a retention time of the sample effluent, each absorbance spectrum of the series of absorbance spectra being composed of a set of absorbance data with respect to wavelengths of light passing through the sample;

b) constructing a chromatogram of the sample using the series of absorbance spectra;

c) detecting a peak section including an object component of the sample effluent in the chromatogram in real time;

d) calculating a similarity value between an absorbance spectrum of each of the plurality of time points and a standard absorbance spectrum of the object component in real time, wherein the similarity value is calculated in the similarity calculating step based on an angle between an absorbance spectrum vector corresponding to the absorbance spectrum and a standard spectrum vector corresponding to the standard absorbance spectrum;

e) calculating a threshold value using the absorbance spectrum of each of the plurality of time points, the standard absorbance spectrum and a noise level value of the chromatograph in real time; and f) determining whether a part of the peak section is pure by comparing the similarity value of the absorbance spectrum of the part of the peak section to the threshold value in real time.

11. The method according to claim 10, wherein the similarity value is calculated by a cosine of the angle between the absorbance spectrum vector corresponding to the absorbance spectrum and a standard spectrum vector corresponding to the standard absorbance spectrum.

12. The method according to claim 10, wherein the threshold value is calculated by a cosine of an angle between two outermost tangential lines of an n-dimensional sphere centering an end of the absorbance spectrum vector and another n-dimensional sphere centering an end of the standard spectrum vector.

13. The method according to claim 10, wherein the noise level value used in calculating is obtained from a statistical standard deviation of absorbance values of a baseline section of the chromatogram, the baseline section being a section or sections of the chromatogram excluding a peak section or peak sections.

14. The method according to claim 10, wherein the noise level value used in calculating the threshold value step is obtained from the absorbance values of a baseline section of a chromatogram obtained from a blank sample including no object component.

15. The method according to claim 10, wherein an absorbance spectrum at a top of the peak section is used as the standard absorbance spectrum.

16. The method of claim 10, further comprising separating purer object component from the sample effluent by avoiding time periods when the threshold value is less than the similarity value.

17. The method according to claim 10, wherein a beginning of the peak section is detected when a slope of the chromatogram exceeds a preset value and an end of the peak section is detected when the slope of the chromatogram subsides below another preset value in the peak section detecting step.

18. The method according to claim 17, wherein the noise level value used in calculating the threshold value is obtained from a statistical standard deviation of absorbance values of a baseline section of the chromatogram, the baseline section being a section or sections of the chromatogram detected by using smaller threshold slope values than those used in detecting the peak section.

* * * * *

UNITED STATES PATENT AND TRADEMARK OFFICE
CERTIFICATE OF CORRECTION

PATENT NO. : 5,596,135
DATED : January 21, 1997
INVENTOR(S) : Yasuhiro MITO et al.

It is certified that error appears in the above-indentified patent and that said Letters Patent is hereby corrected as shown below:

On title page, item [54] and col. 1, line 3, change title to read as follows:

APPARATUS FOR AND METHOD OF DETERMINING PURITY OF A PEAK OF A CHROMATOGRAM

Signed and Sealed this

Twenty-fifth Day of March, 1997

Attest:

BRUCE LEHMAN

*Attesting Officer*     *Commissioner of Patents and Trademarks*